(12) United States Patent
Jin et al.

(10) Patent No.: US 7,858,582 B2
(45) Date of Patent: Dec. 28, 2010

(54) OPHTHALMIC HGM-CSF PREPARATION

(75) Inventors: Lei Jin, Changchun (CN); Jin Pei, Changchun (CN); Gang Meng, Changchun (CN); Junmei Hu, Changchun (CN)

(73) Assignee: Genescience Pharmaceuticals Co., Ltd., Changchun, Jilin (CN)

( * ) Notice: Subject to any disclaimer, the term of this patent is extended or adjusted under 35 U.S.C. 154(b) by 0 days.

(21) Appl. No.: 12/067,927

(22) PCT Filed: Jun. 23, 2006

(86) PCT No.: PCT/CN2006/001430

§ 371 (c)(1),
(2), (4) Date: Aug. 26, 2008

(87) PCT Pub. No.: WO2007/036107

PCT Pub. Date: Apr. 5, 2007

(65) Prior Publication Data

US 2009/0156482 A1    Jun. 18, 2009

(30) Foreign Application Priority Data

Sep. 27, 2005 (CN) .................. 2005 1 0105735

(51) Int. Cl.
*A61K 38/27* (2006.01)
*A61K 38/19* (2006.01)
*A61K 9/06* (2006.01)
*A61K 9/08* (2006.01)
*A61P 17/02* (2006.01)

(52) U.S. Cl. .................. 514/7.9; 530/399; 530/351; 424/78.04

(58) Field of Classification Search .................. None
See application file for complete search history.

(56) References Cited

U.S. PATENT DOCUMENTS

| 5,006,509 | A  | * | 4/1991 | Waago ................ 514/12 |
| 5,942,487 | A  | * | 8/1999 | Ogawa et al. .......... 514/2 |
| 6,335,038 | B1 | * | 1/2002 | Cavazza .............. 424/757 |
| 7,026,296 | B2 | * | 4/2006 | Gamache .............. 514/16 |
| 7,335,682 | B2 | * | 2/2008 | Chen et al. ........... 514/453 |
| 2006/0106104 | A1 | * | 5/2006 | Vehige et al. ......... 514/546 |

FOREIGN PATENT DOCUMENTS

| CN | 1519022 A | 8/2004 |
| JP | 7316066 A | 12/1995 |
| WO | WO-97/39768 A1 | 10/1997 |

OTHER PUBLICATIONS

English translation of- CN1519022ATRANS, Nov. 2009.*
International Search Report mailed Nov. 2, 2006 for PCT Application No. PCT/CN2006/001430 filed Jun. 23, 2006, 5 pages.

* cited by examiner

*Primary Examiner*—Lorraine Spector
*Assistant Examiner*—Elly-Gerald Stoica
(74) *Attorney, Agent, or Firm*—Morrison & Foerster LLP

(57) ABSTRACT

The present invention provides an external preparation and the method for produce the same, in which said external preparation comprises recombinant human growth hormone or recombinant human granulocyte macrophage colony-stimulating factor and pharmaceutical acceptable carriers. The present invention also relates to application and usage method in preparing medicaments for treatment of various lesions and ulcers, especially corneal lesions and corneal ulcers.

19 Claims, 2 Drawing Sheets

OPHTHALMIC HGM-CSF PREPARATION

CROSS REFERENCE TO RELATED APPLICATIONS

This application is a U.S. National Phase Application of PCT/CN2006/001430 filed Jun. 23, 2006, which claims priority to China Patent Application No. 200510105735.1 filed Sep. 27, 2005, the contents of which are hereby incorporated by reference in the present disclosure in their entirety.

TECHNICAL FIELD

The present invention relates to medical field, more particularly, the present invention relates to an external preparation and its preparation and use.

BACKGROUND ART

Human growth hormone (hGH) is a non-glycosylated peptide hormone secreted by the eosinophil of human anterior pituitary. hGH has various biological functions, such as influencing the metabolism of sugars, proteins and lipids, and directly influencing the proliferation, differentiation and DNA synthesis of some cells, but the main function is stimulating body growth, including skeletons, muscles, connective tissues, hair and skin. Recombinant Human Growth Hormone (rhGH) is a hydrophilic protein, which comprises two kinds of molecules with different sizes. The molecular weight of the main component is 22 Kda, and the isoelectric points is 4.9, containing 191 amino acid residues, and 4 Cys residues consisting two pairs of disulfide bonds which formed two peptide cycles with different sized. The molecular weight of the rest component of 5%~10% human growth hormone is 20 Kda, containing 176 amino acid residues with lacking 15 amino acid residues on 32~46 positions of 22 Kda recombinant human growth hormone.

In recent years, genetic engineering technology has been applied to produce large quantities of recombinant human growth hormone, which has promoted the research on growth hormone and broadened its clinical application. The usage range expanded from limited to treat the children with pituitary dwarfism whose growth is seriously inhibited originally to treat other diseases. Human growth hormone is mainly used to treat the following diseases:

1) Children with GH defect or other diseases accompany with growth inhibition

Some diseases may cause GH defect during treatment thus influence growth, such as cerebroma, craniopharyngioma and leukemia. When used Lateral cephalogram radiotherapy or whole body radiotherapy to the patients suffered those diseases, which will cause GH defect to influence growth. Treatment with rhGH can make patients to keep growing, but the children patients without treatment can not recover automatically from the GH defect induced by radiotherapy. As to the children suffered from the neuroblastoma, GH is also an effective stimulus for the growth.

Some diseases, such as Turner's Syndrome, Down's Syndrome, also can arose growth inhibition and other symptoms, but the GH level of patients is not obviously abnormal, and GH administration can lessen the symptoms.

2) metabolism change

GH has specific effect on lipid, glucose and protein metabolism. For the children, adults and elders with GH relative defect, it can influence their various metabolism parameters effectively.

3) osteoporosis

GH can increase chondrocytes proliferation, osteoblasts proliferation and activity. GH also can enhance bone function by increasing the calcium absorption from intestines.

4) Functional renal failure

GH can enhance renal function and rescue the growth inhibition due to chronic renal failure.

5) reproductive malfunction

GH is the permissive factor of various gonadotropin hormones, which indicates that GH can be used to treat male or female infertility.

6) Burn

Recently, as GH has the actions of indirectly promoting growth and enhancing metabolism, increasing cellular and humoral immune response and reducing stress response, it has been widely used in treating clinical burn patients, improving postoperative patients' immunity and speeding up wound healing.

Granulocyte macrophage Colony stimulating Factor (GM-CSF) is differentiated from marrow, and separated from bone marrow precursors, with the biological function of stimulating the colony-forming of macrophagocyte and granulocyte. GM-CSF can also stimulate mature macrophagocyte, eosinophil and neutrophil to induce various functional activities. GM-CSF is an acid protein, and has high affinity with the receptor of GM-CSF sensitive cell.

GM-CSF is a kind of acid protein that is produced and secreted by T cell, B cell, macrophagocyte, mastocyte, endothelial cell and fibroblast and so on. Mature rhGm-CSF comprises 127 amino acids, which comes from cutting off signal peptides of 17 amino acids on the protein precursor with 144 amino acids. Its relative molecular weight is 147000 Da and biological activity can resist to glycosylation.

In recent years, as the application of genetic engineering technology is used to produce large quantities of rhGM-CSF, it has promoted the research on growth hormone and broadened its clinical application. It is the most well known by clinical investigators and the product of it is in the market among diversified cell factors. The basic function of GM-CSF is to stimulate the hemopoietic stem cells to proliferate and differentiate the granulocytes and macrophagocyes, and GM-CSF then matures to have phagocytic function. However, the clinical applications of GM-CSF are not so limited but related to many fields.

So far, the applications of rhGM-CSF now include the following aspects:

(1) Application on rhGM-CSF in tumor disease treatment

1) Solid tumor diseases: In clinic, most tumor chemotherapy drugs will increase the toxicity to the marrow hematopoietic function with the dose increase, result in neutrophil granulocyte decrease and infection increase. Researchers have proven that the neutropenia period could be shortened and the infection rate could be declined by additionally using GM-CSF after chemotherapy. At the same time, GM-CSF can induce and enhance the activity of peripheral monocyte macrophage cells killing tumor cells.

2) Leucocythemia: GM-CSF can prompt more interleukin progenitor cells into the cell cycle, which can shorten the duration of chemotherapy patients neutropenia period, increase the killing effect of chemotherapy drugs on leukemia cells, and reduce fever and infection complications.

(2) Aplastic anemia: The use of GM-CSF in aplastic anemia treatment will reduce the patient infection rate by 50%.

(3) Application on GM-CSF in bone marrow transplantation

GM-CSF can accelerate hematopoietic function recovery, significantly accelerate WBC and PMN recovery, lower infection rate and reduce the times of antibiotic infusion so as to reduce hospitalization time; Meanwhile, through the application of rhGM-CSF and other cytokines, the normal hematopoietic stem cell growth can be regulated and promoted.

(4) Application on GM-CSF in anti-infection treatment

As GM-CSF can stimulate hemopoietic stem cells differentiation to granulocyte and macrophage and proliferate the same, and then gradually mature as phagocytosis cells. It can collaborate with clinical treatment of infectious diseases; In addition, during the bacteremia infection and the spread processes of AIDS patients (mycobacterium invade into monocytes macrophages), the use of GM-CS can activate the infected macrophages, thereby inhibit or kill the mycobacterium in cells with synergistic effect of antibiotic treatment.

Based on the plenty of basic and clinical research results, GM-CSF has bright prospects for clinical application as follows:

(1) GM-CSF has the effect of promoting healing of wounds

Animal experiments show that GM-CSF can induce fibroblasts proliferation and the typical muscle cells formation; activate neutrophils and monocytes/macrophages, prompt endothelial cell mitosis and migration, promote the proliferation of keratinocytes and regulate the expression of fibroblasts. Therefore, it plays a very important role in the promotion of wound healing process.

(2) According to the effect characteristics of GM-CSF on the cell cycle and chemotherapy cycle, the application of the cytokines thereby GM-CSF has effects on all growth levels cells in hematopoietic system, therefore, using the application of GM-CSF at a suitable time during chemotherapy periods can significantly reduce toxicity of chemotherapy and enhance the effects of chemotherapy.

(3) GM-CSF's Immunopotentiation Effects

Numerous experiments show that GM-CSF is a high efficiency immune adjuvant, it can enhance the immune response to vaccine (antigen) of the body, so as to strengthen the body's immune resistance to disease through five ways including systemic actions, regional applications, local application, the fusion protein and in vitro cell activation antigen expression.

GH and GM-CSF have special physical and chemical properties, such as being easily decomposed in intestine, and are used as injection in clinical treatment. So far, no external preparation made of rhGH and rhGM-CSF is used in the treatment of various lesions and ulcers, especially in corneal lesion and corneal ulcer.

DISCLOSURE OF THE INVENTION

It is an object of the invention to provide an external preparation.

It is another object of the invention to provide methods for manufacture of the external preparation.

It is further object of the invention to provide the application of recombinant human growth hormone (rhGH) and recombinant human granulocyte macrophage colony-stimulating factor (rhGM-CSF) in treatment of lesion and/or ulcer, in particular, injury to the cornea and/or ulcer drug.

To achieve the above objects, the invention provides an external preparation, which comprises recombinant human growth hormone or recombinant human granulocyte macrophage colony-stimulating factor and the pharmaceutically acceptable carriers, in which the weight percentage of recombinant human growth hormone is preferably 0.015-0.35%, more preferably 0.035-0.3%, and most preferably 0.07-0.14%, or the weight percentage of recombinant human granulocyte macrophage colony-stimulating factor is preferably 0.0003-0.002%, more preferably 0.0005-0.0015%, and most preferably 0.0008-0.0012% and pharmaceutically acceptable carriers.

The above said of pharmaceutically acceptable carriers preferably include one or more of the following components: mannitol, glycerol, sucrose, trehalose, dextran, human serum albumin, cyclodextrin, propylene glycol, sodium bisulfite, sodium sulfite, sodium pyrosulfite, sodium thiosulfate, sodium formaldehyde sulfoxylate, sodium hydroxide, hydrochloric acid, sulfuric acid, citric acid, sodium citrate, boric acid, sodium borate, citric acid, sodium citrate, maleic acid, sodium maleate, histidine, triethanolamine, sodium chloride, glucose, mannitol, sorbic acid, potassium sorbate, phenylethanol, phenoxy ethanol, chlorobutanol, benzalkonium bromide, domiphen, chlorhexidine, phenylmercuric nitrate, thiomersal or p-hydroxybenzoic esters.

The external preparation is preferably used in ophthalmic ophthalmic drops, ophthalmic gel or ophthalmic ointment.

The said ophthalmic drops are comprised with the following components by weight percentage: 0.015-0.35% of growth hormone or 0.0003-0.002% of recombinant human granulocyte macrophage colony-stimulating factor, 0.1-40% of pharmaceutically acceptable carriers and sterile injection water.

The said ophthalmic gel or ophthalmic ointment is comprised with the following components by weight percentage: 0.015-0.35% of growth hormone or 0.0003-0.002% of recombinant human granulocyte macrophage colony-stimulating factor, 30-90% of thickener, 0.1-40% of pharmaceutically acceptable carriers and sterile injection water.

The said thickeners used in ophthalmic gel preferably include one or more of the following components: polyvinyl alcohol, povidone, cellulose derivatives, methyl cellulose, hydroxypropyl methylcellulose, hydroxyethyl cellulose, hydroxypropyl cellulose, carboxymethyl cellulose, carbomer, gum tragacanth, sodium hyaluronate, gelatin, starch, propylene glycol, glycerin, xanthan gum, chitosan, sodium alginate, phospholipids, poloxamer, liquid paraffin, vaseline, carboxymethylcellulose sodium, lanolin, polysorbate, polyoxyethylene, fatty oil, colloidal silicon, aluminum soap or zinc soap.

The said thickener used in ophthalmic ointment preferably includes one or more of the following components: lard, vegetable oil, hydrogenated vegetable oil, sulfated hydrogenated castor oil, vaseline, paraffin, ceresine, liquid paraffin, lanolin, lanolin alcohol, beeswax, white beeswax, cetin, cholesterol, univalent soap, cetol, stearyl alcohol, sodium dodecyl sulfate, sodium octadecyl sulfate, glycerol monostearate, polyglycerol stearate, TWEEN® 20, TWEEN® 21, TWEEN® 40, TWEEN® 60, TWEEN® 61, TWEEN® 65, TWEEN® 80, TWEEN® 81, TWEEN® 85, polyoxyethylene (40) stearate, glycerogelatin, starch glycerol, sodium alginate, polyethylene glycol, methyl cellulose or hydroxymethyl cellulose sodium.

The said pharmaceutically acceptable carrier with setting the quantity of the external preparation as 100%, contains: 0.1-10 (w) % of isotonic regulator, 0-5(w) % of protein stabilizer, 0.5-5(w) % of pH regulator, 0-30(w) % of humectant, 0-0.2(w) % of preservatives and 0-2(w) % of the antioxidant.

The present invention also provides a method for producing the said external used ophthalmic drops including the following steps (calculated by weight percentage): adding 0.1-40% of pharmaceutically acceptable carriers to the solution containing 0.015-0.35% of recombinant human growth hormone or 0.0003-0.002% of recombinant human granulocyte macrophage colony-stimulating factor, and adding sterile water for injection until certain quantity, then uniform-mixing and sterilizing.

The present invention also provides a methods for producing the said ophthalmic gel or ophthalmic ointment including the following steps (calculated by weight percentage): melting 30-90% thickener as the matrix, adding 0.1-40% the pharmaceutically acceptable carriers to the melted matrix and sterile water for injection, then uniform-mixing and sterilizing. Thereafter, at room temperature, adding a solution containing 0-5% sterilized protein stabilizer and 0.015-0.35% recombinant human growth hormone or 0.0003-0.002% recombinant human granulocyte macrophage cell colony-stimulating factor, adding sterile water for injection to make up, and uniform mixing.

The present invention also provides the application of the said external preparation in preparing medicament for treatment of skin lesions and/or ulcer.

The said lesions and/or ulcer are preferably corneal trauma or corneal ulcer.

The said corneal trauma is preferably aseptic corneal perforation or ulcer.

The usage of the said external preparation preferably combines the external preparation containing recombinant human growth hormone or recombinant human granulocyte macrophage colony-stimulating factor with the agent selected from pharmacy with epithelium and stromal adhesion promotion, antibiotics and artificial tears to administrate, more preferably, the external preparation contains recombinant human growth hormone or recombinant human granulocyte macrophage colony-stimulating factor with the compound selected from dexamethasone, fluorometholone ophthalmic drops, tarivid ophthalmic drops, atropine ophthalmic drops or artificial tears.

The advantages of the said external preparation according to the present invention are as follows:

1. The preparation is uniform transparent semi-solid, possessing the characteristics of water-soluble, and can protect local tissue of the body;

2. The preparation can form a transparent film after spreading on the skin, with strong attachment, no oily, which will not contaminate the clothing and can be washed by water;

3. The preparation is well coupling with the skin, releasing rapidly, taking effect rapidly and lasting for a long time;

4. The preparation can absorb tissue exudates, do not interfere the normal function of the skin with less viscosity, benefit to drug (especially water-soluble drug) release.

5. The patients using rhGM, rhGM-CSF has not shown any toxic reaction during long-term monitor. Limited local application results in less preparation entering into blood few complication and high safety.

BEST MODES FOR CARRYING OUT THE INVENTION

Figure 1:
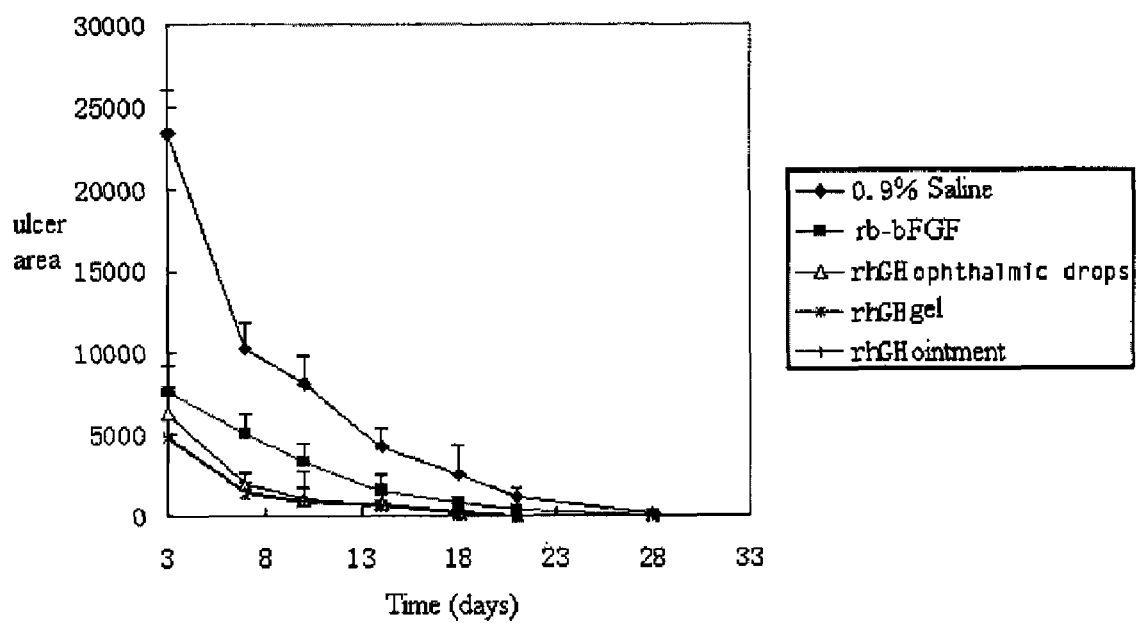
FIG. 1 depicts observation results of the external recombinant human growth hormone and the positive and negative control groups during treatment of corneal ulcers at different time.

In order to understand the present invention more clearly, hereinafter, the use in pharmaceutical of the present invention will be described in detail with pharmacodynamic test by using the recombinant human growth hormone and recombinant human granulocyte macrophage colony-stimulating factor external preparation in the treatment of corneal injury, corneal ulcers and skin ulcers. As the eye agent requests the highest standards in topical formulations, the invention uses ophthalmic preparation as an example to illustrate, but does not limited thereto. For other external preparation, the person skilled in the art can use the conventional technology to prepare.

In the external preparation of the invention, the said recombinant human growth hormone (rhGH) or recombinant human granulocyte macrophage colony-stimulating factor (rhGM-CSF) (produced by Changchun Kinsey LTD.) is the safe rhGH and rhGM-CSF through genetic engineering to be listed with the product names of "Saizeng" and "Jinlei Saiyuan". Their physical and chemical properties are fully in conformity with the requirements of the "People's Republic of China Pharmacopoeia" (2005 version). "rb-bFGF" with the Name "recombinant bovine basic fibroblast growth factor (fusion protein) ophthalmic drops" are purchased from Zhuhai Dongda Biopharmaceutical Company Limited.

The invention will be specifically illustrated and explained by examples as follows.

Ophthalmic Drops

Example 1

Added 1 g albumin to 20 ml aqueous solution containing 200 mg rhGH or 2.0 mg rhGM-CSF, and added 1 g mannitol and 2 g glycerol, then adjusted to pH 6.5 by 5% citric acid solution and fixed volume to 100 ml by adding sterile water for injection. After stirring uniformly, sterilized by 0.2 μm membrane to get the rhGH ophthalmic drops or rhGM-CSF ophthalmic drops.

Example 2

Added 0.5 g glucan to 20 ml aqueous solution containing 150 mg rhGH or 1.2 mg rhGM-CSF, and added 0.5 g mannitol and 5 g glycerol, then adjusted to pH 6.5 by 10% boric acid solution and fixed volume to 100 ml by adding sterile water for injection. After stirring uniformly, sterilized by 0.2 μm membrane to get the rhGH ophthalmic drops or rhGM-CSF ophthalmic drops.

Ophthalmic Gel

Example 3

Added 0.39 Carbomer 934, 0.05 g potassium sorbate, 0.1 g poloxamer and 70 ml water to weighted container with a high-speed mixing, adjusted to pH 5.5 with 1M sodium hydroxide solution, and sterilized at 115° C. for 20 minutes. After cooling to room temperate, added degermed solution containing 0.5 g albumin and 75 mg rhGH or 0.5 g albumin and 0.5 mg rhGM-CSF, and sterile water for injection to fix volume to 100 ml. Stirring uniformly and loading separately to get rhGH ophthalmic gel or rhGM-CSF ophthalmic gel.

Example 4

Added 1 g sodium carboxymethyl cellulose, 0.15 g sorbic acid, 0.2 g TWEEN® 80 and 70 ml water to weighted container, swelled overnight and sterilized at 115° C. for 20 minutes. After cooling to room temperate, added degermed solution containing 1 g glucan and 70 mg rhGH or 1 g glucan and 2.0 mg rhGM-CSF, and sterile water for injection to fix volume to 100 ml. Stirring uniformly and loading separately to get rhGH ophthalmic gel or rhGM-CSF ophthalmic gel.

Example 5

Added 1 g methyl cellulose, 0.1 g poloxamer and 70 ml water to weighted container, swelled overnight and sterilized at 115° C. for 20 minutes. After cooling to room temperate, added degermed solution containing 0.5 g albumin and 35 mg rhGH or 0.5 g albumin and 0.75 mg rhGM-CSF, and sterile water for injection to fix volume to 100 ml. Stirring uniformly and loading separately to get rhGH ophthalmic gel or rhGM-CSF ophthalmic gel.

Example 6

Added 0.8 g hydroxypropyl methyl cellulose sodium, 0.2 g TWEEN® 80 and 70 ml water to weighted container, swelled overnight and sterilized at 115° C. for 20 minutes. After cooling to room temperate, add degermed solution containing 2 g albumin and 350 mg rhGH or 2 g albumin and 2.0 mg rhGM-CSF, and sterile water for injection to fix volume to 100 ml. Stirring uniformly and loading separately to get rhGH ophthalmic gel or rhGM-CSF ophthalmic gel.

Example 7

Added 0.1 g sodium hyaluronate, 0.1 g poloxamer and 70 ml water to weighted container, swelled overnight and sterilized by 0.2 μm membrane, added degermed solution containing 0.5 g albumin and 125 mg rhGH or 0.5 g albumin and 1 mg rhGM-CSF, and sterile water for injection to fix volume to 100 ml. Stirring uniformly and loading separately to get rhGH ophthalmic gel or rhGM-CSF ophthalmic gel.

Example 8

Added 1 g gum tragacanth, 1.0 g sorbic acid, 0.1 g poloxamer, 2 g glycerol and 70 ml water to weighted container, swelled overnight and sterilized at 115° C. for 20 minutes. After cooling to room temperate, added degermed solution containing 1.5 g albumin and 175 mg rhGH solution or 1.5 g albumin and 1.25 mg rhGM-CSF, and sterile water for injection to fix volume to 100 ml. Stirring uniformly and loading separately to get rhGH ophthalmic gel or rhGM-CSF ophthalmic gel.

Example 9

Added 1.5 g sodium alginate, 0.15 g sorbic acid, 0.1 g poloxamer and 70 ml water to weighted container, swelled overnight and sterilized at 115° C. for 20 minutes. After cooling to room temperate, added degermed solution containing 2 g glucan and 250 mg rhGH or 2 g glucan and 1.75 mg rhGM-CSF, and sterile water for injection to fix volume to 100 ml. Stirring uniformly and loading separately to get rhGH ophthalmic gel or rhGM-CSF ophthalmic gel.

Example 10

Added 0.2 g sodium hyaluronate, 0.1 g poloxamer 188, 0.75 g histidine and 70 ml water to weighted container, swelled overnight. After sterilized by 0.2 μm membrane, added degermed solution containing 130 mg rhGH or 1 mg rhGM-CSF, and sterile water for injection to fix volume to 100 ml. Stirring uniformly and loading separately to get rhGH ophthalmic gel or rhGM-CSF ophthalmic gel.

Example 11

Added 0.1 g sodium hyaluronate, 0.1 g poloxamer 188, 0.03 g ethyl Nipagin ester, 0.6 g histidine and 70 ml water to weighted container, swelled overnight. After sterilized by 0.2 μm membrane, added degermed solution containing 65 mg rhGH or 0.5 mg rhGM-CSF, and sterile water for injection to fix volume to 100 ml. Stirring uniformly and loading separately to get rhGH ophthalmic gel or rhGM-CSF ophthalmic gel.

Example 12

Added 0.4 g of sodium hyaluronate, 0.1 g poloxamer 188, 4.5 g mannitol, 0.7 g borate acid and 70 ml water to weighted container, swelled overnight and sterilized at 115° C. for 20 minutes. After cooling to room temperature, added degermed solution containing 15 mg rhGH or 0.3 mg rhGM-CSF, and sterile water for injection to fix volume to 100 ml. Stirring uniformly and loading separately to get rhGH ophthalmic gel or rhGM-CSF ophthalmic gel.

Example 13

Added 0.25 g of sodium hyaluronate, 0.15 g poloxamer 188, 3.0 g mannitol, 0.02 g ethyl Nipagin ester, 1.0 g citrate and 70 ml water to weighted container, swelled overnight and sterilized at 115° C. for 20 minutes. After cooling to room temperature, added degermed solution containing 350 mg rhGH or 2 mg rhGM-CSF, and sterile water for injection to fix volume to 100 ml. Stirring uniformly and loading separately to get rhGH ophthalmic gel or rhGM-CSF ophthalmic gel.

Example 14

Added 0.2 g of sodium hyaluronate, 0.1 g poloxamer 188, 0.70 g histidine and 70 ml water to weighted container, swelled overnight. After sterilized by 0.2 μm membrane, added degermed solution containing 150 mg rhGH or 1.2 mg rhGM-CSF, and sterile water for injection to fix volume to 100 ml. Stirring uniformly and loading separately to get rhGH ophthalmic gel or rhGM-CSF ophthalmic gel.

Ophthalmic Ointment

Example 15

Added 60 g liquid paraffin, 20 g Vaseline, 0.1 g poloxamer, 0.15 g sorbic acid to weighted container, heated to 60° C. to melt them. Sterilized the mixture at 121° C. for 30 minutes. when the temperature dropped to 40° C., added degermed solution containing 1 g albumin and 200 mg rhGH or 1 g albumin and 1.5 mg rhGM-CSF, and sterile water for injection to fix volume to 100 ml. Stirring uniformly and loading separately to get rhGH ophthalmic ointment or rhGM-CSF ophthalmic ointment.

Example 16

Added 70 g yellow Vaseline, 10 g liquid paraffin, 0.1 g poloxamer and 0.15 g sorbic acid to weighted container, heated to 60° C. to melt them. Sterilized the mixture at 121° C. for 30 minutes, when the temperature dropped to 40° C., added degermed solution containing 0.5 g albumin and 30 mg rhGH or 0.5 g albumin and 0.3 mg rhGM-CSF, and sterile water for injection to fix volume to 100 ml. Stirring uniformly and loading separately to get rhGH ophthalmic ointment or rhGM-CSF ophthalmic ointment.

Example 17

Added 60 g Vaseline, 10 g lanolin, 10 g liquid paraffin, and 0.15 g sorbic acid to weighted container, heated to 60° C. to melt them. Sterilized the mixture at 121° C. for 30 minutes, when the temperature dropped to 40° C., added degermed solution containing 1.5 g albumin and 250 mg rhGH or 1.5 g albumin and 1.25 mg rhGM-CSF, and sterile water for injection to fix volume to 100 ml. Stirring uniformly and loading separately to get rhGH ophthalmic ointment or rhGM-CSF ophthalmic ointment.

Example 18

Added 60 g polyethylene glycol 400, 20 g stearyl alcohol, 0.1 g poloxamer, and 0.15 g sorbic acid to weighted container, heated to 60° C. to melt them. Sterilized the mixture at 121° C. for 30 minutes, when the temperature dropped to 40° C., added degermed solution containing 1 g albumin and 150 mg rhGH or 1 g albumin and 1 mg rhGM-CSF, and sterile water for injection to fix volume to 100 ml. Stirring uniformly and loading separately to get rhGH ophthalmic ointment or rhGM-CSF ophthalmic ointment.

Example 19

Added 60 g hydrogenated vegetable oil, 15 g paraffin oil, 8 g castor oil and 0.15 g sorbic acid to weighted container, heated to 60° C. to melt them. Sterilized the mixture at 121° C. for 30 minutes, when the temperature dropped to 40° C., added degermed solution containing 1 g albumin and 100 mg rhGH or 1 g albumin and 0.75 mg rhGM-CSF, and sterile water for injection to fix volume to 100 ml. Stirring uniformly and loading separately to get rhGH ophthalmic ointment or rhGM-CSF ophthalmic ointment.

Example 20

Added 13.5 g cetol, 10 g lanolin, 10 g vaseline, 20 g liquid paraffin and 0.15 g sorbic acid to weighted container, heated to 60° C. to melt them. Sterilized the mixture at 121° C. for 30 minutes, when the temperature dropped to 40° C., added degermed solution containing 0.75 g albumin and 75 mg rhGH or 0.75 g albumin and 0.55 mg rhGM-CSF, and sterile water for injection to fix volume to 100 ml. Stirring uniformly and loading separately to get rhGH ophthalmic ointment or rhGM-CSF ophthalmic ointment.

Treatment for cornea injure and corneal ulcer by rhGH and rhGH-CSF for external use 1. Methods of Experiment (1) Preparation of Animal Model of Rabbit Sterile Corneal Ulcer A rabbit was hocused by injecting 0.5 mg/Kg of ketamine and 0.5 mg/Kg of diazepam. Operation used micro-instruments under a microscope was under sterile condition. A sterile drilling lesion with Ø5 mm in size and 0.1 mm in depth (about ⅓ of cornea thickness), and a corneal ulcer was made in the center of right cornea of the rabbit with Ø5 mm ring drill. Administering some tobrex after operation.

(2) Animal Grouping

64 New Zealand rabbits were divided into 8 groups stochastically, with 8 in each group. The first group was saline group, the second one was positive control (Recombinant Bovine Basic Fibroblast Growth Factor, rb-bFGF in short) group, the third group was rhGH ophthalmic drops group of example 1, the forth group was rhGM-CSF ophthalmic drops group of example 2, the fifth group was rhGH gel group of example 14, the sixth group was rhGM-CSF gel group of example 7, the seventh group was fhGH ointment group of example 18, the eighth group was rhGM-CSF ointment group of example 15.

(3) Administration After Operation

Administer tobrex 3 times on the operation day after operation. From the first day after operation, rhGH or rhGM-CSF ophthalmic drops, gel or ointment as described above are applied separately, with 0.9% of saline and rb-bFGF for negative and positive control, specific administration program was as follows:

Group 1: 0.9% saline 3 times/day and tobrex 3 times/day

Group 2: rb-bFGF 3 times/day and tobrex 3 times/day

Group 3: rhGH ophthalmic drops 3 times/day and tobrex 3 times/day

Group 4: rhGM-CSF ophthalmic drops 3 times/day and tobrex 3 times/day

Group 5: rhGH gel 3 times/day and tobrex 3 times/day

Group 6: rhGM-CSF gel 3 times/day and tobrex 3 times/day

Group 7: rhGH ointment 3 times/day and tobrex 3 times/day

Group 8: rhGM-CSF ointment 3 times/day and tobrex 3 times/day

Observed and recorded cicatrization situations of corneal ulcer of 64 rabbits in 8 groups on the 3rd, 7th, 14th, 18th, 21st, and 28th day after operation, results of which were shown in FIG. 1.

(4) Observation and Photo Record

Observed and recorded cicatrization situations of corneal ulcer of 64 rabbits in 8 groups on the 3rd, 7th, 14th, 18th, 21st, and 28th day after operation, including: size change of corneal ulcer area, infection and perforation or not. Selected 2 rabbits from each group and recorded in KODAK films with TOPCON slit lamp photo system, scanned them into a computer for image analysis.

2. Experiment Results 3.1 Standard of Cicatrization:

(1) partial healing: No obvious ulcer, only epidermis coarseness or punctuated infection. (2) complete healing: no obvious ulcer, no epidermic coarseness or punctuated infection.

Figure 2:
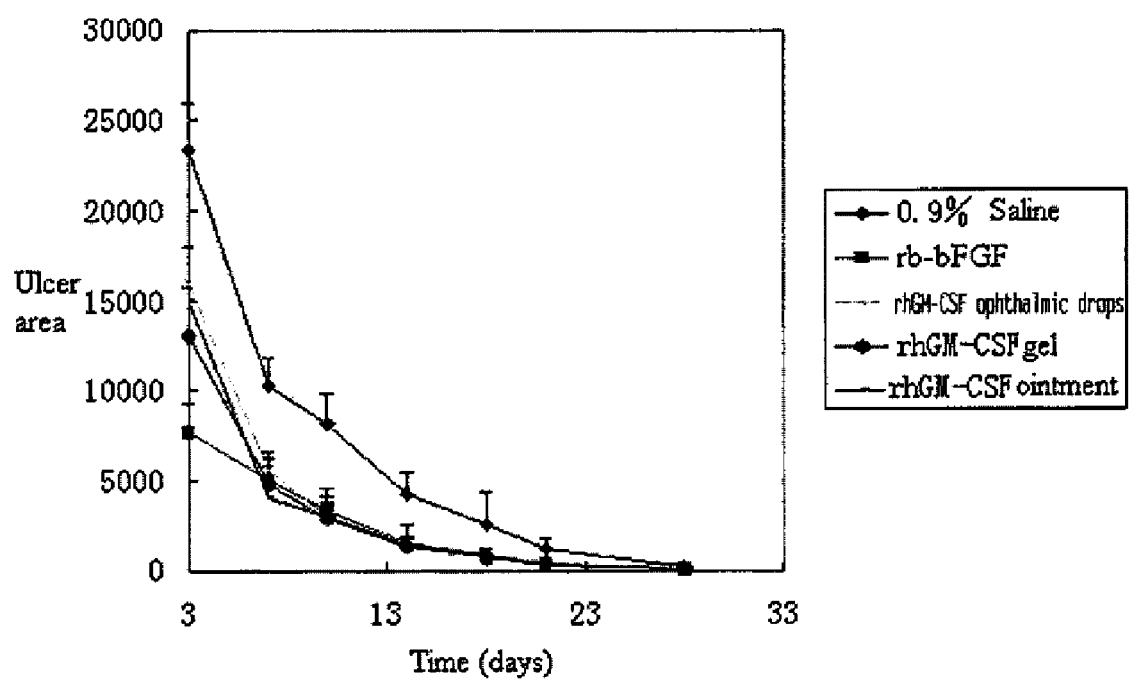
FIG. 2 depicts observation results of the external recombinant human granulocyte macrophage colony-stimulating factor and the positive and negative control groups in the treatment of corneal ulcers at different time.

3.2 Observation Results:

No infection in 64 eyes of 8 groups. Measurement records of width and height of rabbit ulcer area are shown in table 1 and 2, FIGS. 1 and 2.

TABLE 1

Observation results at different time of treating corneal ulcer with rhGH, rhGM-CSF, positive and negative control groups for external use

| | Medicament grouping | Animal amount (n) | average area (mean) | Standard deviation (S.D.) |
|---|---|---|---|---|
| 3 days after operation | 0.9% saline | 8 | 23339.28 | 2624.90 |
| | rb-bFGF | 8 | 7646.97 | 1626.46 |
| | rhGH ophthalmic drops | 8 | 6307.87 | 1523.00 |
| | rhGM-CSF ophthalmic drops | 8 | 16022.39 | 1923.99 |
| | rhGH gel | 8 | 4838.72 | 961.12 |
| | rhGM-CSF gel | 8 | 13033.77 | 2683.11 |
| | rhGH ointment | 8 | 4927.15 | 1086.78 |
| | rhGM-CSF ointment | 8 | 14996.48 | 3687.25 |
| 7 days after operation | 0.9% saline | 8 | 10282.49 | 1573.62 |
| | rb-bFGF | 8 | 5033.08 | 1234.53 |
| | rhGH ophthalmic drops | 8 | 1989.93 | 710.32 |
| | rhGM-CSF ophthalmic drops | 8 | 5563.76 | 962.13 |
| | rhGH gel | 8 | 1368.17 | 667.28 |
| | rhGM-CSF gel | 8 | 4750.10 | 1012.16 |
| | rhGH ointment | 8 | 1489.23 | 596.35 |
| | rhGM-CSF ointment | 8 | 4057.26 | 885.32 |
| 10 days after operation | 0.9% saline | 8 | 8163.14 | 1721.08 |
| | rb-bFGF | 8 | 3347.86 | 1163.13 |
| | rhGH ophthalmic drops | 8 | 1010.07 | 669.12 |
| | rhGM-CSF ophthalmic drops | 8 | 3026.35 | 1049.94 |
| | rhGH gel | 8 | 809.69 | 309.28 |
| | rhGM-CSF gel | 8 | 2897.12 | 918.88 |
| | rhGH ointment | 8 | 959.68 | 1857.36 |
| | rhGM-CSF ointment | 8 | 2986.38 | 1256.35 |
| 14 days after operation | 0.9% saline | 8 | 4275.93 | 1116.76 |
| | rb-bFGF | 8 | 1562.49 | 953.58 |
| | rhGH ophthalmic drops | 8 | 758.32 | 177.28 |
| | rhGM-CSF ophthalmic drops | 8 | 1404.51 | 521.62 |
| | rhGH gel | 8 | 554.94 | 139.40 |
| | rhGM-CSF gel | 8 | 1354.19 | 444.56 |
| | rhGH ointment | 8 | 576.82 | 172.85 |
| | rhGM-CSF ointment | 8 | 1377.28 | 757.26 |

TABLE 2

| | | | | |
|---|---|---|---|---|
| 18 days after operation | 0.9% saline | 8 | 2551.12 | 1802.16 |
| | rb-bFGF | 8 | 798.54 | 367.59 |
| | rhGH ophthalmic drops | 8 | 218.44 | 95.23 |
| | rhGM-CSF ophthalmic drops | 8 | 819.35 | 122.52 |
| | rhGH gel | 8 | 89.33 | 24.79 |
| | rhGM-CSF gel | 8 | 723.90 | 198.41 |
| | rhGH ointment | 8 | 105.23 | 58.28 |
| | rhGM-CSF ointment | 8 | 846.2385 | 105.23 |
| 21 days after operation | 0.9% saline | 8 | 1185.96 | 595.69 |
| | rb-bFGF | 8 | 370.59 | 95.38 |
| | rhGH ophthalmic drops | 8 | 50.14 | 8.50 |
| | rhGM-CSF ophthalmic drops | 8 | 457.1241 | 224.05 |
| | rhGH gel | 8 | 2.37 | 0.39 |
| | rhGM-CSF gel | 8 | 342.5578 | 122.23 |
| | rhGH ointment | 8 | 2.59 | 0.96 |
| | rhGM-CSF ointment | 8 | 315.69 | 74.65 |
| 28 days after operation | 0.9% saline | 8 | 560.75 | 165.26 |
| | rb-bFGF | 8 | 141.4382 | 32.85 |
| | rhGH ophthalmic drops | 8 | 11.54 | 0.11 |
| | rhGM-CSF ophthalmic drops | 8 | 156.54 | 58.75 |
| | rhGH gel | 8 | 2.03 | 0.82 |
| | rhGM-CSF gel | 8 | 130.19 | 73.57 |
| | rhGH ointment | 8 | 3.21 | 0.91 |
| | rhGM-CSF ointment | 8 | 125.65 | 40.25 |

Group 1: Cornea area gradually decreased from the 7th day; 1 eye partially healed on the 18th day; 4 eyes partially healed on the 21st day; 4 eyes partially healed and 4 eyes completely healed until experiment finished on the 28th day.

Group 2: Cornea area gradually decreased from the 3rd day; 1 eye partially healed on the 14th day; 3 eyes partially healed on the 18th day; 3 eyes partially healed and 2 eyes completely healed on the 21st day; until experiment finished on the 28th day, 2 eyes partially healed and 6 eyes completely healed.

Group 3: Cornea area obviously decreased from the 3rd day; 1 eye partially healed on the 7th day; 2 eyes partially healed on the 10th day; 3 eyes partially healed and 5 eyes completely healed on the 14th day; 1 eye partially healed and 7 eyes completely healed on the 18th day; 2 eyes partially healed and 6 eyes completely healed on the 21st day; until experiment finished on the 28th day, 8 eyes completely healed.

Group 4: Cornea area gradually decreased from the 3rd day; 1 eye partially healed on the 7th day; 1 eye partially healed on the 10th day; 3 eyes partially healed and 1 eye completely healed on the 14th day; 4 eye partially healed and 2 eyes completely healed on the 18th day; 6 eyes partially healed and 2 eyes completely healed on the 21st day; until experiment finished on the 28th day 5 eye partially healed and 3 eyes completely healed.

Group 5: Cornea area obviously decreased from the 3rd day; 3 eyes partially healed on the 7th day; 3 eyes partially healed and 2 eyes completely healed on the 10th day; 2 eyes partially healed and 6 eyes completely healed on the 14th day; 6 eyes completely healed on the 18th day; 1 eye partially healed and 7 eyes completely healed on the 21st day; until experiment finished on the 28th day 8 eyes completely healed.

Group 6: Cornea area gradually decreased from the 3rd day; 2 eyes partially healed on the 7th day; 4 eyes partially healed on the 10th day; 3 eyes partially healed and 1 eye completely healed on the 14st day; 6 eyes partially healed and 2 eyes completely healed on the 18th day; 4 eyes partially healed and 4 eyes completely healed on the 21st day; until experiment finished on the 28th day, 1 eye partially healed and 7 eyes completely healed.

Group 7: Cornea area obviously decreased from the 3rd day; 2 eyes partially healed on the 7th day; 2 eyes partially healed and 2 eyes completely healed on the 10th day; 2 eyes partially healed and 6 eyes completely healed on the 14th day; 1 eye partially healed and 7 eyes completely healed on the 18th day; 8 eyes completely healed on the 21st day; until experiment finished on the 28th day, 8 eyes completely healed.

Group 8: Cornea area gradually decreased from the 3rd day; 3 eyes partially healed on the 10th day; 2 eyes partially healed and 3 eyes completely healed on the 14th day; 4 eyes partially healed and 4 eyes completely healed on the 18th day; 3 eyes partially healed and 5 eyes completely healed on the 21st day; until experiment finished on the 28th day, 2 eyes partially healed and 6 eyes completely healed.

3. Experiment Conclusions rhGH and rhGM-CSF were applied for animal model of rabbit sterile corneal ulcer in the present experiment, with local administration, and their treating effect for rabbit shallow corneal ulcer was observed. It can be seen from the experiment results that both rhGH and rhGM-CSF obviously can promote healing of cornea thin matrix and epidermis, specific conclusions are drawn as follows:

3.1 Compared to negative control group, rhGH (ophthalmic drops, gel, ointment), rhGM-CSF (ophthalmic drops, gel, ointment), and rb-bFGF (positive control medicament) obviously decreased healing time of ulcer. There was significant difference between average ulcer area and negative control group. Therefore, it had good practical prospect to use rhGH and rhGM-CSF in treating sterile corneal ulcer.

3.2 In promoting cicatrization of ulcer and inhibiting recrudescence of ulcer, rhGH (ophthalmic drops, gel, ointment) was better than rb-bFGF (positive control group) which has assured effect. There was significant difference in average ulcer areas. Compared to rb-bFGF (positive control group) rhGM-CSF (ophthalmic drops, gel, ointment) had similar effect to cicatrization of sterile corneal ulcer, and there was no significant difference in average ulcer areas.

3.3 In promoting cicatrization of ulcer, external preparation (ophthalmic drops, gel, ointment) of rhGH and rhGM-CSF had slightly better effect in the form of gel and ointment than that of liquid preparation. However, statistically, there was no significant difference.

3.4 In the period of experiment observation, recrudescence occurred on individual experiment rabbit in individual experiment group, that was, epidermis damage or enlargement of ulcer area appeared again after ulcer healed or decreased in size, which had some relationship with pathological development of thin layer ulcer cicatrization of rabbit cornea. It has been found that the adhesive effect of normal cornea epidermis and matrix had important significance to maintain integrity of cornea surface, in which the compound structure of matrix membrane took main role in maintaining the close adhesion. After cornea epidermis was removed together with matrix membrane and thin layer matrix, although epidermis layer may quickly cover ulcer surface in 4 days, it still could not form close connection with lower matrix within 8 weeks or longer time. Consequently, slight hurt or friction may lead to exfoliation of epidermis again. Therefore, the delay of formation of adhesion between epidermis and matrix cause the recrudescence of ulcer. It suggested that the using of medicament for promoting adhesion of epidermis and matrix would effectively prevent recrudescence in treating shallow corneal ulcer.

Effect of External rhGH and rhGM-CSF for Skin Ulcer 48 patients with mouth ulcer aged between 10-42 years old, in which 22 are males and 26 are females, were divided into 2 groups stochastically, and were respectively treated with cataplasm containing 800 μg/ml of rhGH ointment and 3 mg/ml of dexamethasone or cataplasm containing only 3 mg/ml of dexamethasone. They were continuously administered 3 times per day for 3 days. Results were shown in table 3.

TABLE 3

|  | $4^{th}$ day | $6^{th}$ day | $8^{th}$ day | $10^{th}$ day | Average time |
|---|---|---|---|---|---|
| rhGH + dexamethasone | 8 healed | 19 healed | All healed | All healed | 5.5 days |
| dexamethasone | 6 healed | 13 healed | 20 healed | All healed | 6.5 days |

From the results in table 3, it can be seen that cicatrization of ulcer area may be accelerated through combinative use of administration with growth hormone and dexamethasone.

The invention claimed is:

1. An ophthalmic preparation, which comprises the following components by percentage of weight:
   0.001-0.0015% of recombinant human granulocyte macrophage-colony stimulating factor;
   a pharmaceutically acceptable carrier, in which said pharmaceutically acceptable carrier comprises, by weight of said ophthalmic preparation, 0.1-0.5% of protein stabilizer, and 0.15-0.5% of preservatives; and
   0.2-90% of thickener.

2. An ophthalmic preparation as claimed in claim 1, in which said pharmaceutically acceptable carrier comprises at least one compound selected from the group consisting of: mannitol, glycerol, sucrose, trehalose, dextran, human serum albumin, cyclodextrin, propylene glycol, sodium bisulfite, sodium sulfite, sodium pyrosulfite, sodium thiosulfate, sodium formaldehyde sulfoxylate, sodium hydroxide, hydrochloric acid, sulfuric acid, citric acid, sodium citrate, boric acid, sodium borate, citric acid, sodium citrate, maleic acid, sodium maleate, histidine, triethanolamine, sodium chloride, glucose, mannitol, sorbic acid, potassium sorbate, phenylethanol, phenoxy ethanol, chlorobutanol, benzalkonium bromide, domiphen, chlorhexidine, phenylmercuric nitrate, thiomersal, and p-hydroxybenzoic esters.

3. An ophthalmic preparation as claimed in claim 1, in which said pharmaceutically acceptable carrier comprises 0.1% of protein stabilizer by weight.

4. An ophthalmic preparation as claimed in claim 1, in which said pharmaceutically acceptable carrier comprises 0.5% of protein stabilizer by weight.

5. An ophthalmic preparation as claimed in claim 1, in which said pharmaceutically acceptable carrier comprises 0.15% of preservatives by weight.

6. An ophthalmic preparation as claimed in claim 1, in which said pharmaceutically acceptable carrier comprises 0.5% of preservatives by weight.

7. An ophthalmic preparation as claimed in claim 1, in which said ophthalmic preparation comprises 0.2% of thickener.

8. An ophthalmic preparation as claimed in claim 1, in which said ophthalmic preparation comprises 80% of thickener.

9. An ophthalmic preparation as claimed in claim 1, in which said thickener comprises at least one component selected from the group consisting of: polyvinyl alcohol, povidone, cellulose derivatives, methyl cellulose, hydroxypropyl methylcellulose, hydroxyethyl cellulose, hydroxypropyl cellulose, carboxymethyl cellulose, carbomer, gum tragacanth, sodium hyaluronate, gelatin, starch, propylene glycol, glycerin, xanthan gum, chitosan, sodium alginate, phospholipids, poloxamer, liquid paraffin, vaseline, carboxymethylcellulose sodium, lanolin, polysorbate, polyoxyethylene, fatty oil, colloidal silicon, aluminum soap, zinc soap, lard, vegetable oil, hydrogenated vegetable oil, sulfated hydrogenated castor oil, vaseline, paraffin, ceresine, liquid paraffin, lanolin, lanolin alcohol, beeswax, white beeswax, cetin, cholesterol, univalent soap, cetol, stearyl alcohol, sodium dodecyl sulfate, sodium octadecyl sulfate, glycerol monostearate, polyglycerol stearate, TWEEN® 20, TWEEN® 21, TWEEN® 40, TWEEN® 60, TWEEN® 61, TWEEN® 65, TWEEN® 80, TWEEN® 81, TWEEN® 85, polyoxyethylene (40) stearate, glycerogelatin, starch glycerol, sodium alginate, polyethylene glycol, methyl cellulose, and hydroxymethyl cellulose sodium.

10. An ophthalmic preparation as claimed in claim 1, in which said pharmaceutically acceptable carrier further comprises 0.5% of isotonic regulator by weight.

11. An ophthalmic preparation as claimed in claim 1, in which said pharmaceutically acceptable carrier further comprises 10% of pH regulator by weight.

12. An ophthalmic preparation as claimed in claim 1, in which said pharmaceutically acceptable carrier further comprises 5% of humectant by weight.

13. An ophthalmic preparation as claimed in claim 1, in which said pharmaceutically acceptable carrier further comprises 0.5% of antioxidant by weight by weight.

14. An ophthalmic preparation as claimed in claim 1, in which said ophthalmic preparation is an ophthalmic drop, and wherein said ophthalmic drop comprises 0.00125% of recombinant human granulocyte macrophage-colony stimulating factor by weight.

15. An ophthalmic preparation as claimed in claim 1, in which said ophthalmic preparation is an ophthalmic gel, and wherein said ophthalmic gel comprises 0.001% of recombinant human granulocyte macrophage-colony stimulating factor by weight.

16. An ophthalmic preparation as claimed in claim 1, in which said ophthalmic preparation is an ophthalmic ointment, and wherein said ophthalmic ointment comprises 0.0015% of recombinant human granulocyte macrophage-colony stimulating factor by weight.

17. An ophthalmic preparation as claimed in claim 1, in which said ophthalmic preparation is an ophthalmic gel, and wherein said ophthalmic gel comprises the following components by weight: 0.001% of recombinant human granulocyte macrophage-colony stimulating factor and 0.2% thickener.

18. An ophthalmic preparation as claimed in claim 1, in which said ophthalmic preparation is an ophthalmic ointment, and wherein said ophthalmic ointment comprises the following components by weight:
- 0.0015% of recombinant human granulocyte macrophage-colony stimulating factor;
- a pharmaceutically acceptable carrier, in which said pharmaceutically acceptable carrier comprises, by weight of said ophthalmic ointment, 0.1% of protein stabilizer and 0.15% of preservative; and
- 80% of thickener.

19. An ophthalmic preparation which is an ophthalmic drop, and wherein said ophthalmic drop comprises the following components by weight:
- 0.00125% of recombinant human granulocyte macrophage-colony stimulating factor; and
- a pharmaceutically acceptable carrier, in which said pharmaceutically acceptable carrier comprises, by weight of said ophthalmic drop, 0.5% of isotonic regulator, 0.1% of protein stabilizer, 10% of pH regulator, 5% of humectant, 0.5% preservatives, and 0.5% of antioxidant.

* * * * *